US010905572B2

(12) United States Patent
Vogel

(10) Patent No.: US 10,905,572 B2
(45) Date of Patent: Feb. 2, 2021

(54) STENT

(71) Applicant: Covidien LP, Mansfield, MA (US)

(72) Inventor: Jeffrey Vogel, Brooklyn Park, MN (US)

(73) Assignee: Covidien LP, Mansfield, MA (US)

( * ) Notice: Subject to any disclaimer, the term of this patent is extended or adjusted under 35 U.S.C. 154(b) by 686 days.

(21) Appl. No.: 15/351,007

(22) Filed: Nov. 14, 2016

(65) Prior Publication Data

US 2018/0133037 A1    May 17, 2018

(51) Int. Cl.
*A61F 2/915*    (2013.01)
*A61F 2/844*    (2013.01)

(52) U.S. Cl.
CPC ............. *A61F 2/915* (2013.01); *A61F 2/844* (2013.01); *A61F 2002/91541* (2013.01); *A61F 2002/91575* (2013.01)

(58) Field of Classification Search
CPC ............ A61F 2/915; A61F 2002/91508; A61F 2002/9516; A61F 2002/91525; A61F 2/95; A61F 2/844; A61F 2002/91541; A61F 2002/91575; A61F 2/82; A61F 2/86; A61F 2/91
See application file for complete search history.

(56) References Cited

U.S. PATENT DOCUMENTS

| | | | |
|---|---|---|---|
| 5,354,308 A * | 10/1994 | Simon | A61F 2/90 606/198 |
| 5,707,386 A | 1/1998 | Schnepp-Pesch et al. | |
| 5,718,713 A | 2/1998 | Frantzen | |
| 5,759,192 A | 6/1998 | Saunders | |
| 5,827,321 A * | 10/1998 | Roubin | A61F 2/91 623/1.16 |
| 5,843,164 A | 12/1998 | Frantzen et al. | |
| 5,843,175 A * | 12/1998 | Frantzen | A61F 2/91 623/1.15 |

(Continued)

FOREIGN PATENT DOCUMENTS

| CN | 1479596 | 3/2004 |
|---|---|---|
| CN | 101385669 | 3/2009 |

(Continued)

OTHER PUBLICATIONS

U.S. Appl. No. 15/351,052, naming Jeffrey Vogel et al., filed Nov. 14, 2016.

(Continued)

*Primary Examiner* — Vi X Nguyen

(74) *Attorney, Agent, or Firm* — Shumaker & Sieffert, PA

(57) ABSTRACT

A stent may include a stent body defining a longitudinal axis and proximal and distal ends. The stent body may be expandable from a compressed configuration to an expanded configuration. In some examples, the stent body may include a plurality of stent segments. The stent segments may include a first end segment and a second end segment on opposite ends of the stent body and at least one intermediate segment disposed between the first end segment and the second end segment. Each stent segment may define a plurality of cells. Each stent segment may define a plurality of peaks and valleys. The plurality of cells defined by the first end segment may alternate about the circumference of the stent between larger cells and smaller cells.

40 Claims, 8 Drawing Sheets

(56) References Cited

U.S. PATENT DOCUMENTS

| | | | |
|---|---|---|---|
| 5,860,999 A | 1/1999 | Schnepp-Pesch et al. | |
| 5,902,317 A * | 5/1999 | Kleshinski | A61F 2/90 606/198 |
| 6,042,606 A * | 3/2000 | Frantzen | A61F 2/91 623/1.18 |
| 6,106,548 A * | 8/2000 | Roubin | A61F 2/91 623/1.15 |
| 6,190,406 B1 | 2/2001 | Duerig et al. | |
| 6,306,141 B1 | 10/2001 | Jervis | |
| 6,312,459 B1 * | 11/2001 | Huang | A61F 2/91 623/1.15 |
| 6,348,065 B1 | 2/2002 | Brown et al. | |
| 6,358,274 B1 | 3/2002 | Thompson | |
| 6,558,415 B2 * | 5/2003 | Thompson | A61F 2/915 623/1.15 |
| 6,623,518 B2 | 9/2003 | Thompson et al. | |
| 6,699,278 B2 | 3/2004 | Fischel et al. | |
| 6,755,856 B2 | 6/2004 | Fierens et al. | |
| 6,814,746 B2 | 11/2004 | Thompson et al. | |
| 6,818,014 B2 | 11/2004 | Brown et al. | |
| 6,863,685 B2 | 3/2005 | Davila et al. | |
| 6,913,619 B2 | 7/2005 | Brown et al. | |
| 6,962,603 B1 | 11/2005 | Brown et al. | |
| 6,981,986 B1 * | 1/2006 | Brown | A61F 2/91 623/1.16 |
| 7,147,660 B2 | 12/2006 | Chobotov et al. | |
| 7,147,661 B2 | 12/2006 | Chobotov et al. | |
| 7,316,711 B2 | 1/2008 | Allen et al. | |
| 7,329,277 B2 | 2/2008 | Addonizio et al. | |
| 7,473,275 B2 | 1/2009 | Marquez | |
| 7,625,400 B2 | 12/2009 | Bowe et al. | |
| 7,655,033 B2 | 2/2010 | Fearnot et al. | |
| 7,753,948 B2 | 7/2010 | Roeder et al. | |
| 7,766,954 B2 | 8/2010 | Chobotov et al. | |
| 7,993,388 B2 | 8/2011 | Lee et al. | |
| 8,114,149 B2 | 2/2012 | Fischell et al. | |
| 8,167,927 B2 | 5/2012 | Chobotov | |
| 8,187,396 B2 | 5/2012 | Parker | |
| 8,211,162 B2 | 7/2012 | Tischler et al. | |
| 8,236,043 B2 | 8/2012 | Caro et al. | |
| 8,241,346 B2 | 8/2012 | Chobotov | |
| 8,328,864 B2 | 12/2012 | Niermann | |
| 8,328,865 B2 * | 12/2012 | Bales, Jr. | A61F 2/915 623/1.18 |
| 8,333,799 B2 * | 12/2012 | Bales, Jr. | A61F 2/88 623/1.18 |
| 8,382,816 B2 | 2/2013 | Pollock et al. | |
| 8,597,343 B2 | 12/2013 | Bliss et al. | |
| 8,628,565 B2 | 1/2014 | Ta et al. | |
| 8,658,081 B2 | 2/2014 | Gale et al. | |
| 9,180,031 B2 | 11/2015 | Vogel et al. | |
| 9,259,335 B2 | 2/2016 | Vogel et al. | |
| 9,610,180 B2 * | 4/2017 | Cam | A61B 17/12118 |
| 2004/0138737 A1 * | 7/2004 | Davidson | A61F 2/82 623/1.35 |
| 2004/0167635 A1 | 8/2004 | Yachia et al. | |
| 2006/0015173 A1 * | 1/2006 | Clifford | A61F 2/91 623/1.16 |
| 2007/0050011 A1 * | 3/2007 | Klein | A61F 2/91 623/1.16 |
| 2007/0061003 A1 * | 3/2007 | Shmulewitz | A61F 2/91 623/1.16 |
| 2007/0100434 A1 | 5/2007 | Gregorich et al. | |
| 2007/0239263 A1 | 10/2007 | Fliedner | |
| 2008/0221661 A1 | 9/2008 | Bidne et al. | |
| 2009/0105809 A1 * | 4/2009 | Lee | A61F 2/91 623/1.17 |
| 2009/0118810 A1 * | 5/2009 | Klein | A61F 2/91 623/1.11 |
| 2010/0137974 A1 | 6/2010 | Chouinard et al. | |
| 2012/0165920 A1 | 6/2012 | Meyer et al. | |
| 2012/0226346 A1 * | 9/2012 | Boismier | A61F 2/915 623/1.16 |
| 2014/0067045 A1 * | 3/2014 | Wack | A61F 2/91 623/1.16 |
| 2014/0128959 A1 | 5/2014 | Gale et al. | |
| 2014/0277379 A1 * | 9/2014 | Vogel | A61F 2/82 623/1.16 |
| 2014/0277380 A1 * | 9/2014 | Vogel | A61F 2/86 623/1.16 |
| 2015/0105852 A1 | 4/2015 | Noffke et al. | |
| 2015/0297378 A1 | 10/2015 | Senness et al. | |
| 2016/0022453 A1 | 1/2016 | Vogel et al. | |
| 2016/0120670 A1 | 5/2016 | Vogel et al. | |

FOREIGN PATENT DOCUMENTS

| | | |
|---|---|---|
| CN | 101516291 | 8/2009 |
| DE | 10144430 A1 | 3/2003 |
| DE | 102007060497 A1 | 6/2009 |
| EP | 1523959 A2 | 4/2005 |
| WO | 3725937 A1 | 7/1997 |
| WO | 2004/028571 A2 | 4/2004 |
| WO | 2007005800 A1 | 1/2007 |
| WO | 2007013102 A1 | 2/2007 |
| WO | 2008005535 A2 | 1/2008 |
| WO | 2009/137993 A1 | 11/2009 |
| WO | 2012096716 A2 | 7/2012 |
| WO | 2012143731 A1 | 10/2012 |

OTHER PUBLICATIONS

U.S. Appl. No. 15/351,082, naming Jeffrey Vogel et al., filed Nov. 14, 2016.

PCT/US2017/061208, The International Search Report and The Written Opinion of the International Searching Authority, dated Feb. 16, 2018, 14pgs.

PCT/US2017/061209, The International Search Report and The Written Opinion of the International Searching Authority, dated Feb. 16, 2018, 14 pgs.

PCT/US2017/061210, The International Search Report and The Written Opinion of the International Searching Authority, dated Feb. 16, 2018, 14 pgs.

* cited by examiner

STENT

TECHNICAL FIELD

This disclosure relates to a medical device, and, in particular, to a stent.

BACKGROUND

Stents are widely used for numerous medical applications where the stent is placed in the lumen of a subject and expanded. Stents may be used in the coronary or the peripheral vasculature, as well as other body lumens. In some examples, stents are metal, tubular structures which are passed through a body lumen in a collapsed state. At the point of an obstruction or other deployment site in the body lumen, the stent is expanded to support the lumen. Stents may be self-expanding or balloon-expandable. Self-expanding stents may be inserted in a constrained state into a body lumen via a delivery device and released, such that the unconstrained stent is free to radially expand. A balloon-expandable stent may be positioned on a balloon of a balloon catheter, and the stent may be expanded at the deployment site through inflation of the balloon.

SUMMARY

In some aspects, this disclosure describes example stents, which may be vascular stents or arterial stents. A stent may include a stent body defining a longitudinal axis and proximal and distal ends. The stent body may be expandable from a compressed configuration to an expanded configuration. The stent body may include a plurality of stent segments, including a first end segment and a second end segment on opposite ends of the stent body and at least one intermediate segment disposed between the first end segment and the second end segment. Each stent segment may define a plurality of cells and a plurality of peaks and valleys. The plurality of cells defined by the first end segment may alternate about the circumference of the stent between larger cells and smaller cells.

In some examples, the example stents may be formed by a method including selecting an appropriate diameter tube, forming the stent pattern described above in a tubular member to form the stent body, incrementally expanding and heat setting the tubular member, and heat setting the tube at its final diameter.

Clause 1: In some examples, a stent comprises a stent body defining a longitudinal axis and proximal and distal ends. The stent body is expandable from a compressed configuration to an expanded configuration. The stent body includes a plurality of stent segments. The stent segments include a first end segment and a second end segment on opposite ends of the stent body and at least one intermediate segment disposed between the first end segment and the second end segment. Each stent segment defines a plurality of cells. Each stent segment defines a plurality of peaks and valleys. The plurality of cells defined by the first end segment alternate about the circumference of the stent between larger cells and smaller cells.

Clause 2: In some examples of the stent of clause 1, the plurality of cells defined by the at least one intermediate segment are substantially equal in size.

Clause 3: In some examples of the stent of clause 1 or 2, the at least one intermediate segment defines only x number of peaks and valleys, and the first end segment defines at least x+1 number of peaks and valleys.

Clause 4: In some examples of the stent of clause 3, the first end segment includes only $$\frac{5}{4}x$$

number of peaks and valleys.

Clause 5: In some examples of the stent of clause 2 or 3, the second end segment defines at least x+1 number of peaks and valleys.

Clause 6: In some examples of the stent of any of clauses 3-5, the second send segment defines only $$\frac{5}{4}x$$

number of peaks and valleys.

Clause 7: In some examples of the stent of any of clauses 1-6, the at least one intermediate segment defines only y number of cells; and the first end segment defines at least y+1 number of cells.

Clause 8: In some examples of the stent of clause 7, the second end segment defines at least y+1 number of cells.

Clause 9: In some examples of the stent of clause 1, the at least one intermediate segment defines only x number of peaks and valleys, and wherein the first end segment defines only x number of peaks and valleys.

Clause 10: In some examples of the stent of clause 9, the second end segment defines only x number of peaks and valleys.

Clause 11: In some examples of the stent of any of clauses 1, 9, and 10, the plurality of cells defined by the second end segment alternate about the circumference of the stent between larger cells and smaller cells.

Clause 12: In some examples, a method of forming a stent comprises forming a stent pattern in a tubular member to form a stent body defining a longitudinal axis and proximal and distal ends. The stent body is expandable from a compressed configuration to an expanded configuration. The stent body includes a plurality of stent segments. The stent segments include a first end segment and a second end segment on opposite ends of the stent body and at least one intermediate segment disposed between the first end segment and the second end segment. Each stent segment defines a plurality of cells. Each stent segment defines a plurality of peaks and valleys. The plurality of cells defined by the first end segment alternate about the circumference of the stent between larger cells and smaller cells.

Clause 13: In some examples of the method of clause 12, the tubular member comprises shape-memory material.

Clause 14: In some examples of the method of clause 12 or 13, the method further comprises incrementally expanding and heat setting the tubular member.

Clause 15: In some examples of the method of any of clauses 12-14, the plurality of cells defined by the at least one intermediate segment are substantially equal in size.

Clause 16: In some examples of the method of any of clauses 12-15, the at least one intermediate segment defines only x number of peaks and valleys, and wherein the first end segment defines at least x+1 number of peaks and valleys.

Clause 17: In some examples of the method of clause 16, the first end segment includes only $$\frac{5}{4}x$$

number of peaks and valleys.

Clause 18: In some examples of the method of clauses 16 or 17, the second end segment defines at least x+1 number of peaks and valleys.

Clause 19: In some examples of the method of clause any of clauses 16-18, the second send segment defines only $$\frac{5}{4}x$$

number of peaks and valleys.

Clause 20: In some examples of the method of any of clauses 12-19, the at least one intermediate segment defines only y number of cells; and the first end segment defines at least y+1 number of cells.

Clause 21: In some examples of the method of clause 20, the second end segment defines at least y+1 number of cells.

Clause 22: In some examples of the method of clause 12, the at least one intermediate segment defines only x number of peaks and valleys, and wherein the first end segment defines only x number of peaks and valleys.

Clause 23: In some examples of the method of clause 22, the second end segment defines only x number of peaks and valleys.

Clause 24: In some examples of the method of any of clauses 12, 22, and 23, the plurality of cells defined by the second end segment alternate about the circumference of the stent between larger cells and smaller cells.

Clause 25: In some examples, a method comprises advancing a distal end of a catheter to a treatment site within a patient, wherein stent is disposed within the catheter; and releasing the stent from the catheter at the treatment site. The stent comprises a stent body defining a longitudinal axis and proximal and distal ends. The stent body is expandable from a compressed configuration to an expanded configuration. The stent body including a plurality of stent segments. The stent segments include a first end segment and a second end segment on opposite ends of the stent body and at least one intermediate segment disposed between the first end segment and the second end segment. Each stent segment defines a plurality of cells. Each stent segment defines a plurality of peaks and valleys. The plurality of cells defined by the first end segment alternate about the circumference of the stent between larger cells and smaller cells.

Clause 26: In some examples of the method of clause 25, the method further comprises inserting a guide member into a body lumen of the patient; and advancing the distal end of the catheter to the treatment site over the guide member.

Clause 27: In some examples of the method of clause 24 or 25, the plurality of cells defined by the at least one intermediate segment are substantially equal in size.

Clause 28: In some examples of the method of any of clauses 25-27, the method the at least one intermediate segment defines only x number of peaks and valleys, and wherein the first end segment defines at least x+1 number of peaks and valleys.

Clause 29: In some examples of the method of clause 28, the first end segment defines only $$\frac{5}{4}x$$

number of peaks and valleys.

Clause 30: In some examples of the method of clause 28 or 29, the second end segment defines at least x+1 number of peaks and valleys.

Clause 31: In some examples of the method of clause 30, the second send segment defines only $$\frac{5}{4}x$$

number of peaks and valleys.

Clause 32: In some examples of the method of any of clauses 25-31, the at least one intermediate segment defines only y number of cells, and the first end segment defines at least y+1 number of cells.

Clause 33: In some examples of the method of clause 32, the second end segment defines at least y+1 number of cells.

Clause 34: In some examples of the method of clause 25, the at least one intermediate segment defines only x number of peaks and valleys, and wherein the first end segment defines only x number of peaks and valleys.

Clause 35: In some examples of the method of clause 34, the second end segment defines only x number of peaks and valleys.

Clause 36: In some examples of the method of any of clauses 25, 34 and 35, the plurality of cells defined by the second end segment alternate about the circumference of the stent between larger cells and smaller cells.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
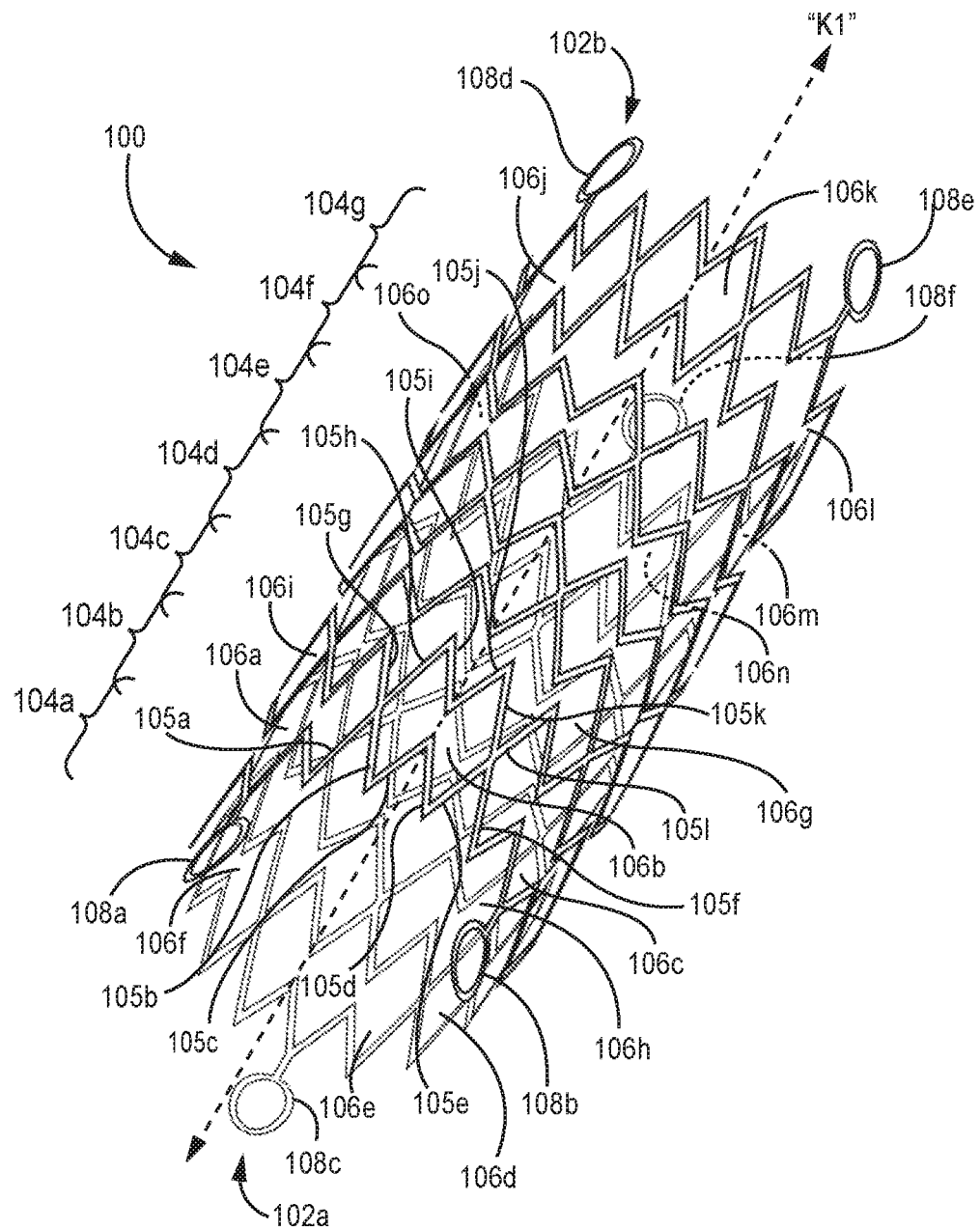
FIG. 1A is a perspective view of an example stent in an expanded condition.

A medical stent, e.g., a vascular stent or an arterial stent, may be configured such that certain mechanical characteristics of the stent, such as lateral and radial strength, fracture resistance, and uniform strain distribution, are balanced with stent flexibility in both the longitudinal and radial directions. A stent may be flexible in order to accommodate movement at the implantation site within a patient. For example, a stent may be positioned within a subject's vasculature at or near a subject's joint (e.g., hip, knee, elbow, etc.). In these regions, the stent is subjected to torsion, bending and other mechanical stress. Moreover, stents for use in the venous system such as inferior vena cava (IVC), common iliac, external iliac, and common femoral veins regions require high strength and maximum flexibility.

In some cases, an end of a stent may have different performance requirements than the middle of the stent. Flexibility, radial force (e.g., force in radially outward directions from a center axis of the stent) and lateral force (e.g., force in a single lateral direction), and durability requirements may each be somewhat different for the end of the stent than for the middle. In addition, the end may play a particularly important role with respect to ease of deployment of the stent in a body lumen of a patient and/or deployment accuracy.

The example stents described herein may accomplish particular technical advantages. For example, the modification of at least one of the end segments of a stent, such that it has a different configuration than the intermediate segments of the stent, including a greater number of cells (e.g., due to a greater number of struts, a greater number of connectors between struts, or both) than the intermediate segments, may improve ease of deployment and deployment accuracy when compared to stents without modification to any of the end segments (with the same configuration in the intermediate segments and the end segments). The configuration of the end segments of the stent may allow the stent to be deployed more smoothly (e.g., may experience less "jump") from a delivery device (e.g., a delivery catheter), which may allow the stent to be more easily, predictably, and accurately deployed in the intended site in a body lumen of a patient without it jumping out of the delivery device (e.g., as an outer sheath is retracted) and away from the intended target site.

Additionally, at least one of the example stents described herein, having more struts in at least one end segment compared to the intermediate segment, may result in reduced radial and lateral forces exhibited by the end segment when compared to stents with end segments having the same number of struts as intermediate segments, such that the diameter transition will be less abrupt when the end of the stent is deployed oversized in a relatively healthy portion of a vein or other body lumen.

The example stents described herein may also accomplish particular technical advantages compared to end segments including the same number of struts but twice the number of evenly sized cells as intermediate segments. For example, the example stents may have increased flexibility over such designs without substantial reduction in radial or lateral force. With increased flexibility in the end segments, overlapped stents may have smoother flexibility transitions in a region of overlap (e.g., defined by end segments of the overlapped stents) and, therefore, improved durability in an overlapped configuration.

In some examples, a stent includes a stent body defining a longitudinal axis and proximal and distal ends. The stent body may be expandable from a compressed configuration to an expanded configuration. The stent body may include a plurality of stent segments, including a first end segment and a second end segment on opposite ends of the stent body and at least one intermediate segment disposed between the first end segment and the second end segment. Each stent segment may define a plurality of cells and a plurality of peaks and valleys. The plurality of cells defined by the first end segment may alternate about the circumference of the stent between larger cells and smaller cells.

In some examples, the example stents may be formed by a method including selecting an appropriate diameter tube, forming the stent pattern described above in a tubular member to form the stent body, incrementally expanding and heat setting the tubular member, and heat setting the tube at its final diameter.

Although the figures below illustrate stents with a particular number of segments, the number of segments may vary depending on the type of interventional procedure.

The stents of the present disclosure may have particular application in an iliofemoral vein of a patient. However, the stents may be used in any suitable location of the vasculature or other body lumen.

Figure 1B:
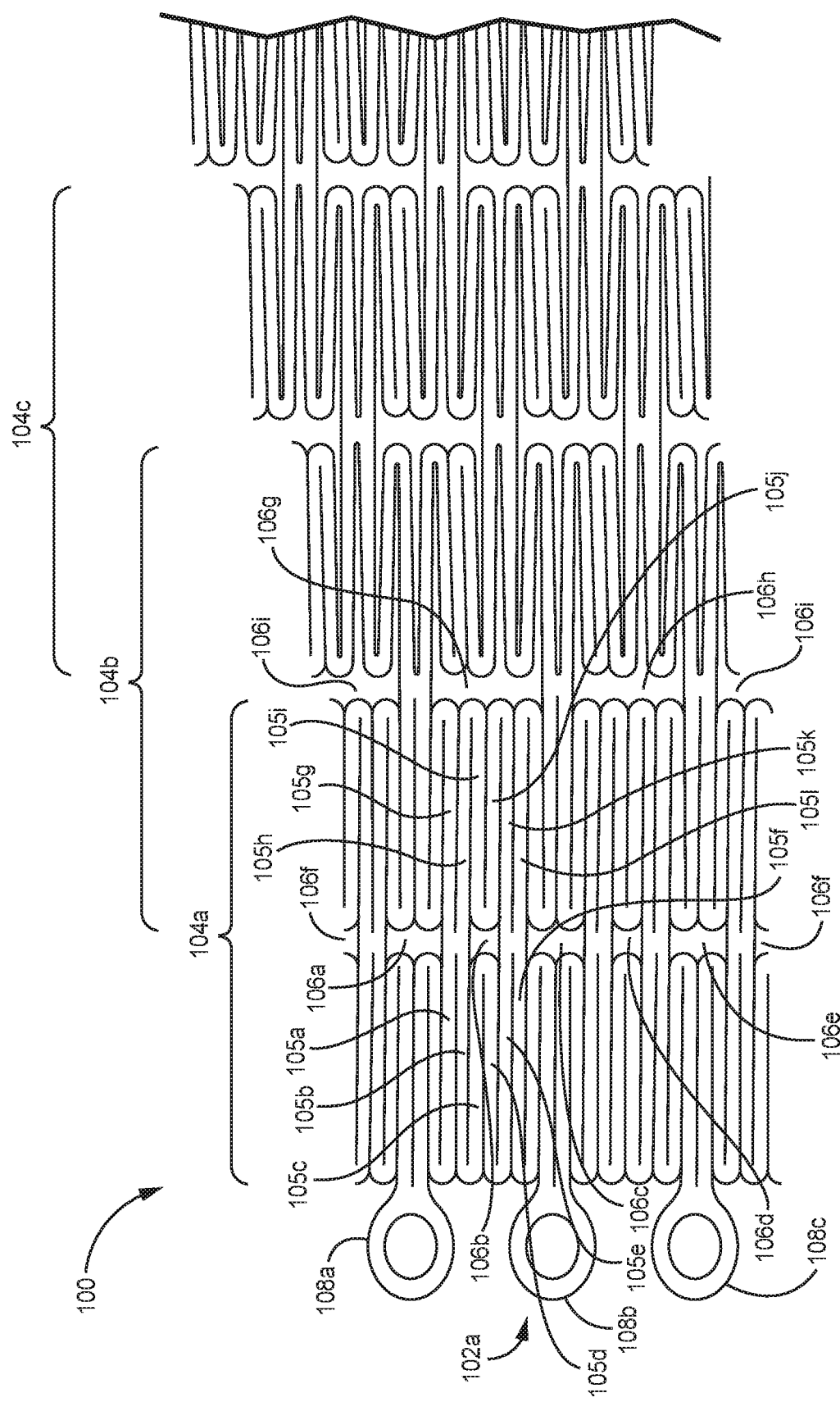
FIG. 1B is a plan view of a portion of the stent of FIG. 1A unrolled, laid flat, and in an unexpanded condition.
Figure 1C:
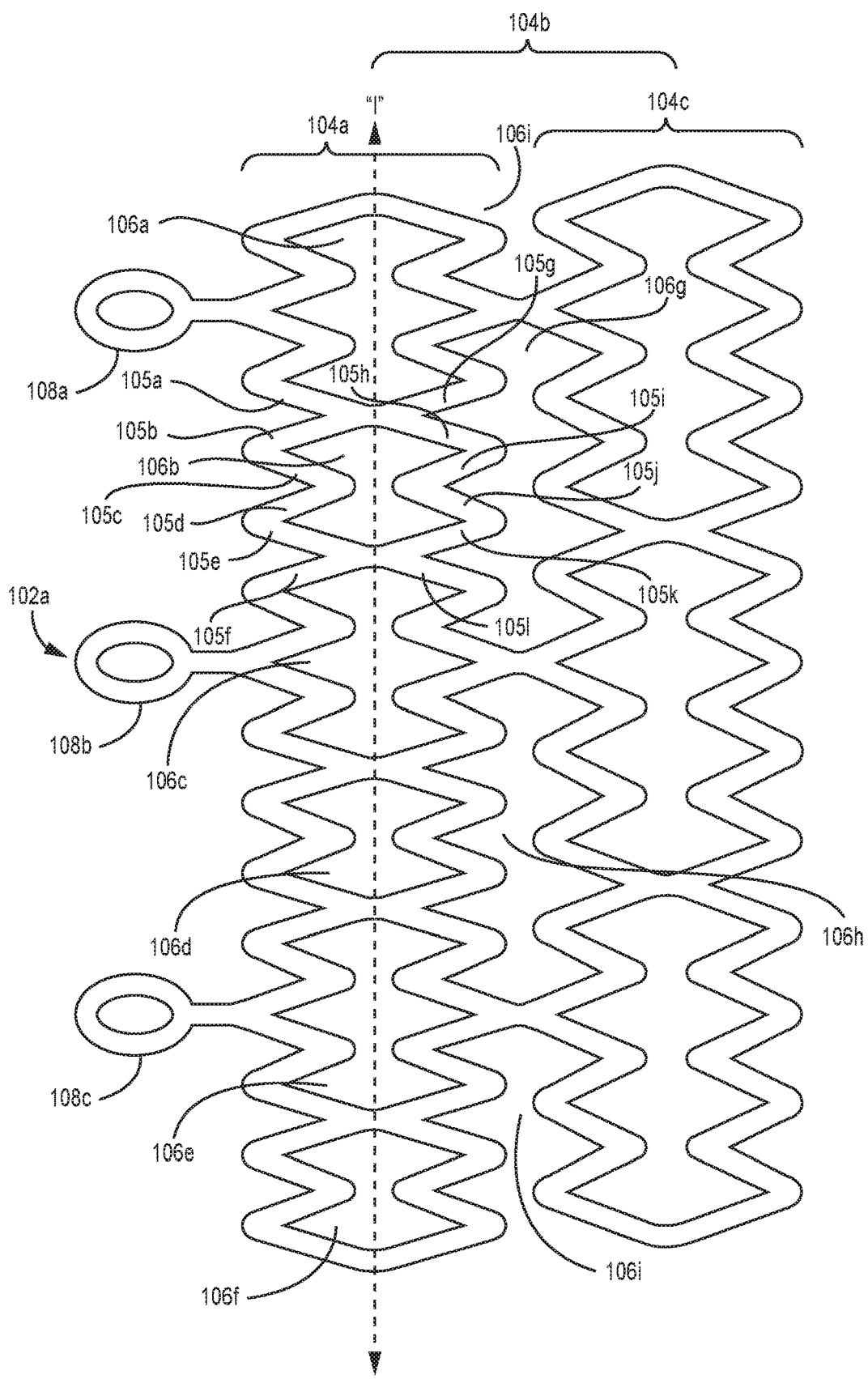
FIG. 1C is a plan view of a portion of the stent of FIG. 1A unrolled, laid flat, and in an expanded condition.

FIG. 1A is a perspective view of an example stent in an expanded condition. FIG. 1B is a plan view of a portion of the stent of FIG. 1A unrolled, laid flat, and in an unexpanded condition. FIG. 1C is a plan view of a portion of the stent of FIG. 1A unrolled, laid flat, and in an expanded condition. In the example shown in FIGS. 1A-1C, the stent comprises a stent body 100 defining a longitudinal axis "k1," a proximal end 102a and a distal end 102b. The stent body 100 may be expandable from a compressed configuration, as shown in FIG. 1B, to an expanded configuration, as shown in FIGS. 1A and 1C.

In a compressed configuration, the stent body 100 may define a smaller profile (e.g., a smaller outer perimeter, which may be an outer diameter in examples in which the stent body 100 is round in cross-section). The stent body 100 may be compressed for, example, before deployment at a treatment site, including when the stent body 100 is being delivered to the treatment site. The compressed configuration of the stent body 100 may allow for a lower profile delivery system, due at least in part to the smaller profile stent body 100, which may increase the ease with which the stent body 100 may be delivered to a treatment site within a body lumen.

In some examples, the stent body 100 may be biased to an expanded configuration but may be compressed and constrained, for example, by a sheath of a delivery catheter until deployment of the stent body 100 from the delivery catheter. For example, the stent body 100 may formed from a shape memory material, such as, but not limited to, a nickel titanium alloy. The stent body 100 may be deployed at a treatment site by, for example, retraction of the sheath of the delivery catheter which may allow for the stent body 100 to expand into the body lumen.

In some examples, the stent body 100 may not be biased to an expanded configuration and may be expanded at the delivery site by, for example, a balloon catheter or another mechanism suitable for expanding the stent body 100 from the compressed configuration to the expanded configuration. For example, the stent body 100 may be formed from stainless steel or another suitable non-self-expanding material.

The stent body 100 may include a plurality of stent segments 104a-104g (collectively referred to herein as "stent segments 104). Each of the stent segments 104 may be defined by a pair of adjacent circumferential rows of struts, where each row of struts extends in a circumferential direction. Adjacent stent segments, such as stent segments 104a and 104b, may share a common row of struts. Example struts are shown as struts 105a-105l in FIGS. 1A-1C, and the struts of the stent body 100 may be collectively referred to as struts 105. Each of the struts 105 may be a substantially straight portion (e.g., a straight or nearly straight member) of the stent body 100 that may join with one or more other struts 105 at a vertex. For example, the strut 105b is a substantially straight portion of the stent body 100 that joins with the struts 105a, 105g, and 105h at one vertex and joins with the strut 105c at another vertex. As another example, the strut 105c is a straight portion of the stent body 100 that joins with the strut 105b at one vertex and joins with the strut 105d at another vertex. In some examples, the struts 105 may each remain substantially straight before and after expansion of the stent body 100. However, the struts 105 may move relative to each other, e.g., pivoting at the vertices relative to adjacent struts, when the stent body 100 expands from the compressed configuration to the expanded configuration.

Although the stent body 100 is illustrated in FIG. 1A as including seven overlapping stent segments 104a-104g and four independent, non-overlapping stent segments 104a, 104c, 104e, and 104g, in other examples, the stent body 100 may include any suitable number of stent segments 104 according to particular needs. For example, in applications requiring a shorter stent, the stent body 100 may include a smaller number of stent segments 104, such as three, four, five, or six stent segments. As another example, in applications requiring a longer stent, the stent body 100 may include a larger number of stent segments 104. In some examples, each of the stent segments 104 may be shorter and/or longer such that a greater or fewer number of total stent segments 104 may result in a stent body 100 with the same length.

The stent segments 104 of the stent body 100 include an end segment 104a located at the proximal end 102a of the stent body 100, and an end segment 104g at the distal end 102b of the stent body 100. Each of the end segments 104a and 104g may be located at an end of the stent body 100 so that it is only adjacent one other stent segment. The stent segments 104 further include at least one intermediate segment 104b-104f disposed between the end segment 104a and the end segment 104g.

Each of the stent segments 104 may define a plurality of cells 106, which may each be a closed cell defined by surrounding struts 105 and each defining a single opening. For example, the end segment 104a may define the cells 106a-106f, the intermediate segment 104b may define the cells 106g-106i, and the end segment 104g may define the cells 106j-106o.

In some examples, the terminal ends 108a-108f are configured to help retain the stent body 100 on a delivery device (e.g., configured to mate with structures on a delivery device). In addition, in some example, one or more terminal ends 108a-108f may be radiopaque or may include radiopaque elements, which may be configured to aid a clinician in visualizing the position of the stent body 100 within a body lumen.

In some examples, the plurality of cells 106a-106f defined by the end segment 104a may alternate about the circumference of the stent body 100 between larger cells 106a, 106c, and 106e and smaller cells 106b, 106d, and 106f. In some examples, the plurality of cells 106g-106i defined by the intermediate segment 104b may be substantially equal in size. In some examples, the plurality of cells 106j-106o defined by the end segment 104g may alternate about the circumference of the stent body 100 between larger cells 106j, 106l, and 106n and smaller cells 106k, 106m, and 106o, similar to the end segment 104a.

Each of the cells 106 may define a plurality of peaks and valleys. A peak may be a vertex that, together with the adjacent struts 105 forming the vertex, points in a distal or proximal direction away from a longitudinal center of the stent segment comprising the cell. For example, the struts 105b and 105c join at a vertex to form a peak pointing in a proximal direction away from a longitudinal center of the stent segment 104a. The longitudinal center of the stent segment 104a is shown by the line labeled "l" in FIG. 1C. As another example, the struts 105h and 105i join at a vertex to form a peak pointing in a distal direction away from the longitudinal center of the stent segment 104a. A valley may be a vertex that, together with the adjacent struts forming the vertex, points in a distal or proximal direction toward the longitudinal center of the stent segment comprising the cell. For example, the struts 105c and 105d join at a vertex to form a valley pointing in a distal direction toward the longitudinal center of the stent segment 104a. As another example, the struts 105i and 105j join at a vertex to form a valley pointing in a proximal direction toward the longitudinal center of the stent segment 104a. In some cases, the vertex of a valley may be located at the longitudinal center of the stent segment comprising the cell. For example, the struts 105a, 105b, 105g, and 105h join at a vertex at the longitudinal center of the stent segment 104a, the struts 105a and 105b form a valley pointing in a distal direction, and the struts 105g and 105h form a valley pointing in a proximal direction.

In some examples, larger cells may be defined by more surrounding struts 105 than smaller cells and may define more peaks and valleys than smaller cells. For example, each of the cells 106a, 106c, and 106e may be defined by twelve surrounding struts and each of the cells 106b, 106d, and 106f may be defined by eight surrounding struts. For example, the cell 106b may be defined by the eight surrounding struts 105b, 105c, 105d, 105e, 105h, 105i, 105j, and 105k. Also for example, each of two opposing sides of each of the cells 106a, 106c, and 106e may define three peaks, two valleys, and two half-valleys and each of two opposing sides of each of the cells 106b, 106d, and 106f may define two peaks, one valley, and two half-valleys. For example, each of two opposing sides of the cell 106b may define two peaks, formed at the vertices between the struts 105b and 105c and between the struts 105d and 105e on one side and formed by the vertices between the struts 105h and 105i and between the struts 105j and 105k on the other side, one valley, formed at the vertex between the struts 105c and 105d on one side and formed by the vertex between the struts 105i and 105j on the other side, and two half valleys, formed by the struts 105b and 105e on one side and by the struts 105h and 105k on the other side. A half-valley may be one half of a valley, as defined by one strut defining the cell, and may combine with another half-valley, as defined by an adjacent strut defining an adjacent cell, to form the valley. For example, the strut 105b may define one half of a valley and the strut 105a may define one half valley, such that the two half-valleys may combine to form a whole valley.

In some examples, at least one of the end segment 104a or the end segment 104g (e.g., one of the end segments 104a or 104g, or both of the end segments 104a and 104g) may define more peaks and valleys than at least one of the intermediate segments 104b-104f. For example, the intermediate segment 104b and/or any of the intermediate segments 104c-104f, may define x number of peaks and valleys and the end segment 104a, the end segment 104g, or both of the end segments 104a, 104g may define at least x+1 number of peaks and valleys. For example, in some examples, the end segment 104a, the end segment 104g, or both of the end segments 104a, 104g may include only $$\frac{5}{4}x$$

number of peaks and valleys. In other examples, the end segment 104a, the end segment 104g, or both of the end segments 104a, 104g may include greater than $$\frac{5}{4}x$$

number of peaks and valleys.

For example, in the illustrated example, each side of each of the intermediate segments 104b-104f (i.e., each circumferential row of struts defining either side of the respective stent segment) defines 24 peaks and valleys, including twelve peaks and twelve valleys, and each side of each of the end segments 104a and 104g defines 30 peaks and valleys, including fifteen peaks and fifteen valleys.

In some examples, at least one of the end segment 104a and the end segment 104g (e.g., one of the end segments 104a or 104g, or both of the end segments 104a and 104g) may define more cells than at least one of the intermediate segments 104b-104f (e.g., one of the end segments 104b-104f, all of the end segments 104b-104f, or some number of end cells between one and all). For example, the intermediate segment 104b and/or any of the intermediate segments 104b-104f, may define y number of cells and the end segment 104a, the end segment 104g, or both of the end segments 104a, 104g may define at least y+1 number of cells. For example, in the illustrated example, the intermediate segment 104b defines the three cells 106g, 106h, and 106i and end segment 104a defines the six cells 106a, 106b, 106c, 106d, 106e, and 106f.

In some examples, each of the end segment 104a and 104g may define more cells than at least one of the intermediate segments 104b-104f. For example, the intermediate segment 104b and/or any of the intermediate segments 104c-104f, may define y number of cells and each of the end segments 104a and 104g may define at least y+1 number of cells. For example, in the illustrated example, the intermediate segment 104b defines the three cells 106g, 106h, and 106i, the end segment 104a defines six cells 106a, 106b, 106c, 106d, 106e, and 106f, and the end segment 104g defines the six cells 106j, 106k, 106l, 106m, 106n, and 106o.

The end segments 104a and 104g of the stent body 100 may have different performance requirements than the middle of the stent body 100. In some cases, it may be desirable to have reduced radial and lateral force (when in the expanded state) at the end segments 104a and 104g relative to the intermediate segments. For example, lower radial and lateral forces at the end segments 104a and 104g may result in a diameter transition that is less abrupt when the end of the stent is deployed oversized in a relatively healthy portion of a vein or other body lumen. In addition, the configuration of the end segments 104a and 104g may influence the ease of deployment of the stent in a body lumen of a patient and/or deployment accuracy.

The pattern of the cells 106 of the end segments 104a and 104g of the stent body 100 as described herein, which have a different configuration than the intermediate segments of the stent body 100, including a greater number of peaks and valleys than the intermediate segments, may reduce radial and lateral forces in the end segments 104a and 104g, when compared to stents with end segments having the same number of struts as intermediate segments, such that the diameter transition will be less abrupt when the distal end 102b of the stent body 100 is deployed oversized in a relatively healthy portion of a vein or other body lumen of a patient. In addition, the pattern of the cells 106 of the end segments 104a and 104g of the stent body 100 as described herein, which have a different configuration than the intermediate segments of the stent body 100, including a greater number cells and a greater number of peaks and valleys than the intermediate segments, may also improve ease of deployment and deployment accuracy of stent 100 compared to stents with the same configuration in the end and intermediate segments. For example, the stent may be deployed more smoothly (e.g., may experience less "jump") such that the stent may be more easily, predictably, and accurately deployed in the intended delivery site within a body lumen of a patient. For example, a greater number of struts and connectors in the end segments 104a and 104g (relative to the intermediate segments) may allow the stent 100 to be smoothly deployed from a delivery device without the stent jumping out of the delivery device and away from the intended target. The greater number of connectors compared to the intermediate segments may increase the stiffness of the end segments 104a and 104g, while the greater number of struts may increase the flexibility of the end segments 104a and 104g.

The pattern of the cells 106 of the end segments 104a and 104g of the stent body 100 as described herein may also accomplish particular technical advantages compared to stents with end segments including the same number of struts but twice the number of evenly sized cells as intermediate segments. For example, the end segments 104a and 104g may have increased flexibility over such designs without substantial reduction in radial force or lateral force. With increased flexibility in the end segments 104a and 104g, overlapped stents may have smoother flexibility transitions in a region of overlap and, therefore, improved durability in an overlapped configuration.

Figure 2A:
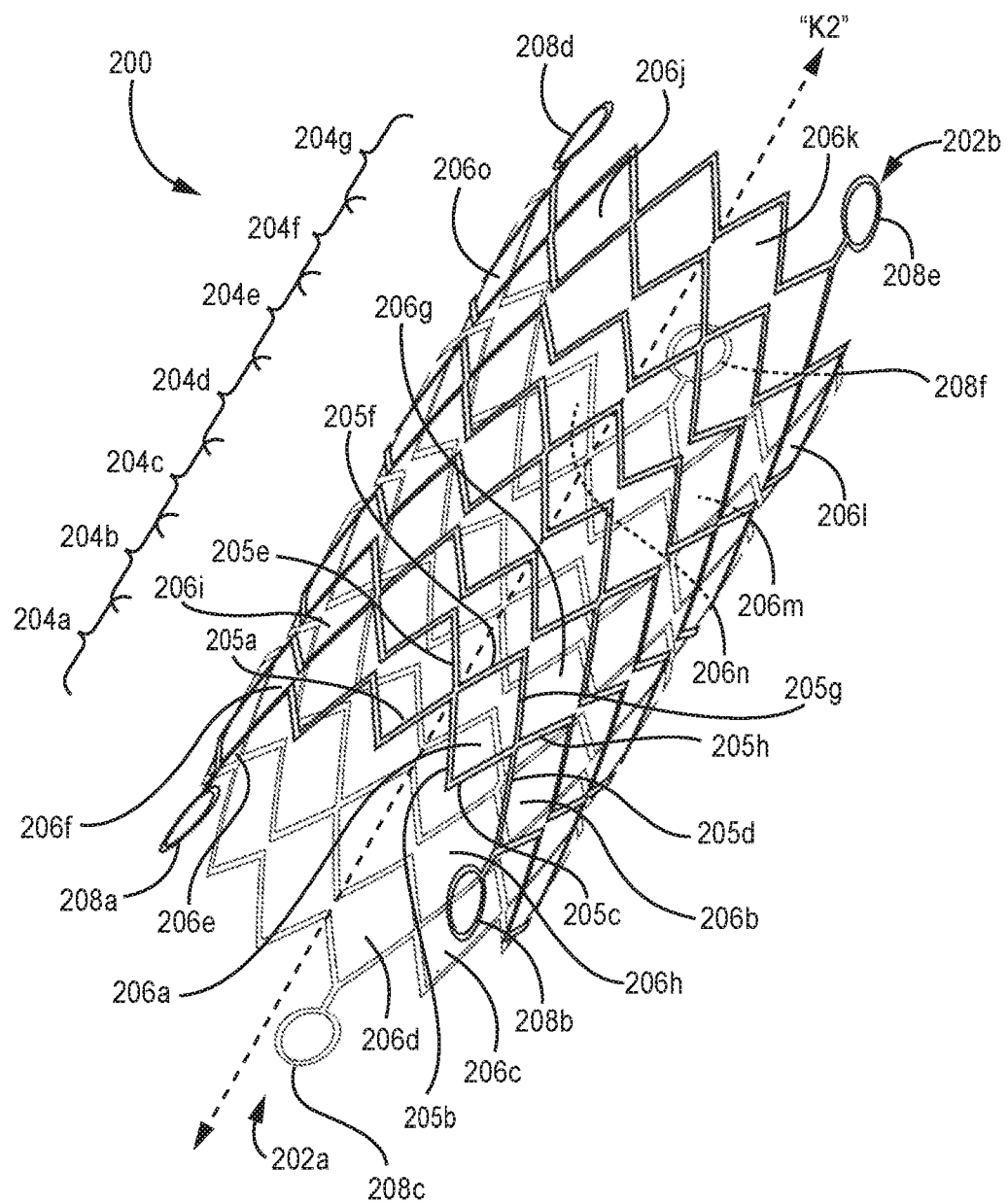
FIG. 2A is a perspective view of another example stent in an expanded condition.
Figure 2B:
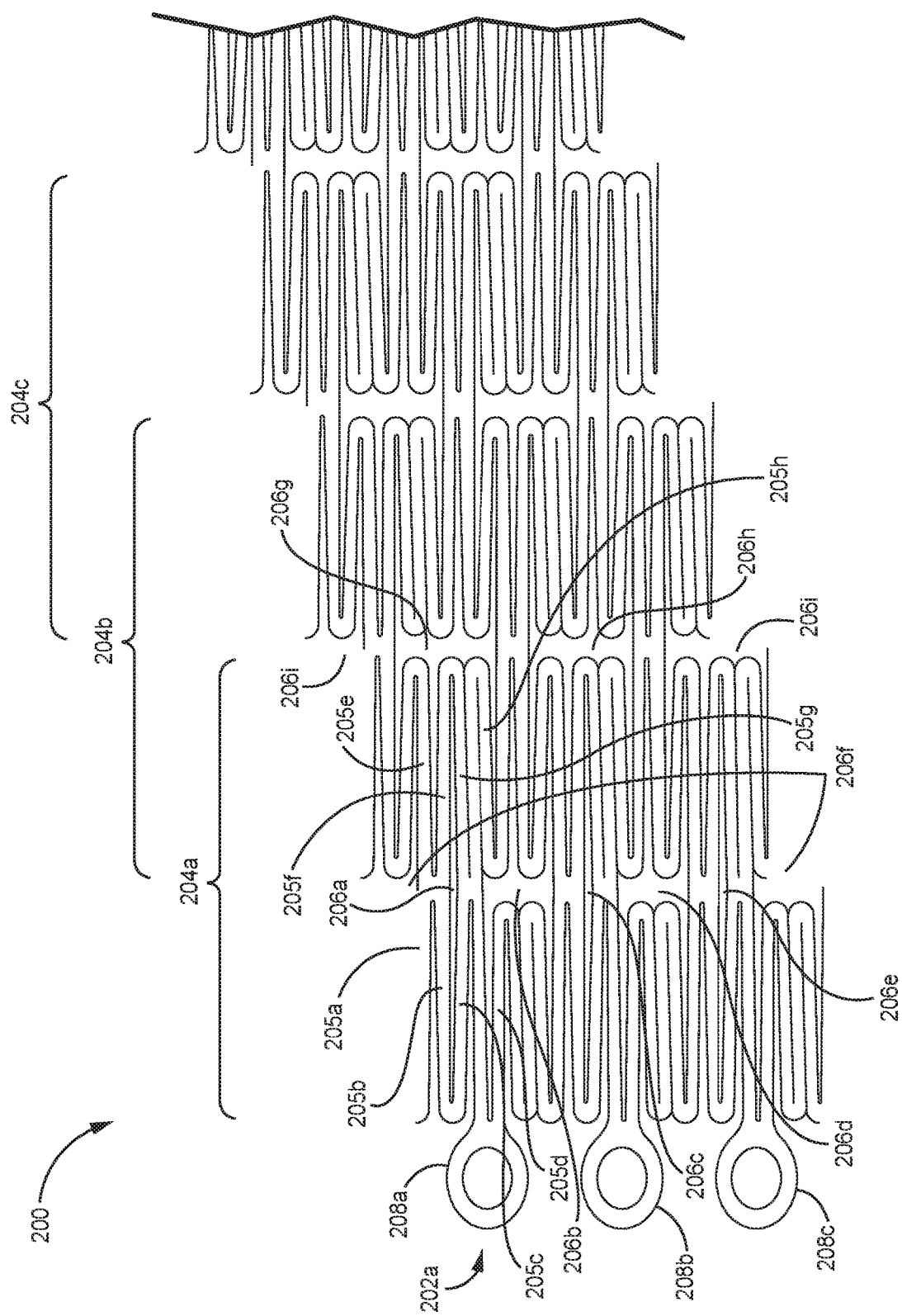
FIG. 2B is a plan view of a portion of the stent of FIG. 2A unrolled, laid flat, and in an unexpanded condition.
Figure 2C:
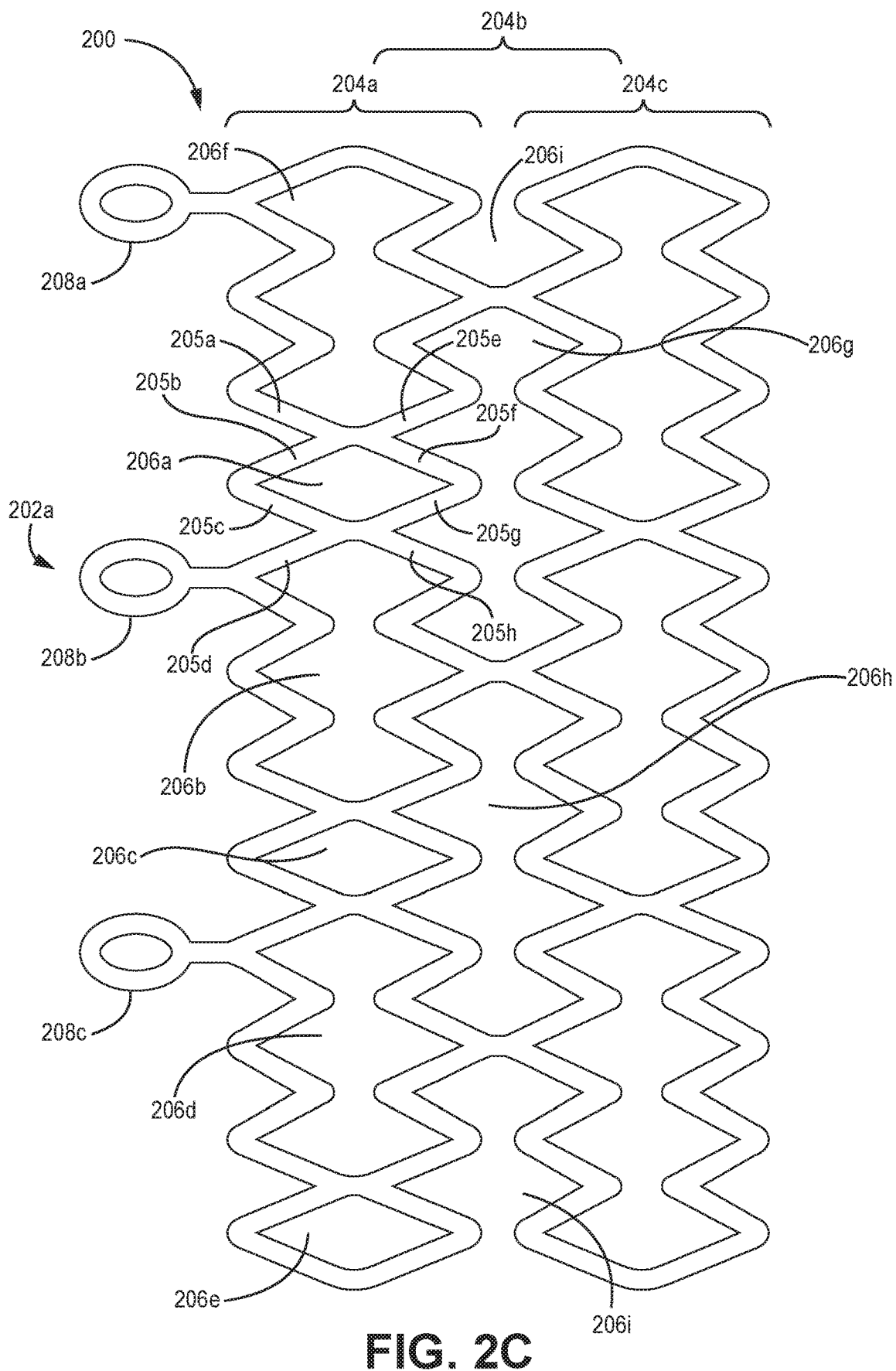
FIG. 2C is a plan view of a portion of the stent of FIG. 2A unrolled, laid flat, and in an expanded condition.

FIG. 2A is a perspective view of another example stent in an expanded condition. FIG. 2B is a plan view of a portion of the stent of FIG. 2A unrolled, laid flat, and in an unexpanded condition. FIG. 2C is a plan view of a portion of the stent of FIG. 2A unrolled, laid flat, and in an expanded condition. In the example shown in FIGS. 2A-2C, the stent comprises a stent body 200 defining a longitudinal axis "k2," a proximal 202a, and a distal end 202b. The stent body 200 may be expandable from a compressed configuration, as shown in FIG. 2B, to an expanded configuration, as shown in FIGS. 2A and 2C. As discussed below, the end segments 204a and 204g of the stent body 200 have a different arrangement of connectors between its struts than the end segments 104a and 104g of the stent body 100.

As with the stent body 100 in FIGS. 1A and 1B, the stent body 200 may be compressed for, example, before deployment, including when delivered to a treatment site. This may allow for easier delivery of the stent body 200 within a body lumen.

In some examples, the stent body 200 may be biased to an expanded configuration but may be compressed and constrained, for example, by a sheath of a delivery catheter until deployment of the stent body 200 from the delivery catheter. The stent body 200 may be deployed at a treatment site by, for example, retraction of the sheath of the delivery catheter which may allow for the stent body 100 to expand into the body lumen.

In some examples, the stent body 200 may not be biased to an expanded configuration and may need to be expanded at the delivery site by, for example, a balloon catheter or another mechanism suitable for expanding the stent body 100 from the compressed configuration to the expanded configuration.

The stent body 200 may include a plurality of stent segments 204a-204g. Each of the stent segments 204 may be defined by a pair of adjacent circumferential rows of struts. Each of the struts 205 may be similar to the struts 105 of the stent body 100, and may each be a substantially straight portion (e.g., a straight or nearly straight member) of the stent body 200 that may join with one or more other struts 205 at a vertex. For example, the strut 205b is a substantially strait portion of the stent body 200 that joins with the struts 205a, 205e, and 205f at one vertex and joins with the strut 205c at another vertex. As another example, the strut 205c is a straight portion of the stent body 200 that joins with the strut 205b at one vertex and joins with the struts 205d, 205g, and 205h at another vertex. Although the stent body 200 is illustrated in FIG. 2A as including seven overlapping stent segments 204a-204g (and four independent, non-overlapping stent segments 204a, 104c, 104e, and 104g), in other examples, the stent body 200 may include any suitable number of stent segments 204 according to particular needs, as discussed with respect to the stent body 100 (FIGS. 1A-1C). For example, in applications requiring a shorter stent, the stent body 200 may include a smaller number of stent segments 204, such as three, four, or five stent segments. As another example, in applications requiring a longer stent, the stent body 200 may include a larger number of stent segments 204. In some examples, each of the stent segments 204 may be shorter and/or longer such that a greater or fewer number of total stent segments 204 may result in a stent body 200 with the same length.

The stent segments 204 of the stent body 200 include an end segment 204a located at the proximal end 202a of the stent body 200, and an end segment 204g at the distal end 202b of the stent body 200. Each of the end segments 204a and 204g may be located at an end of the stent body 200 so that it is only adjacent one other stent segment. The stent segments 204 further include at least one intermediate segment 204b-204f disposed between the end segment 204a and the end segment 204g.

Each of the stent segments 204 may define a plurality of cells 206, which may each be a closed cell defined by surrounding struts 205 and each defining a single opening. For example, the end segment 204a may define the cells 206a-206f, the intermediate segment 204b may define the cells 206g-206i, and the end segment 204g may define the cells 206j-206o, similar to the end segment 204a.

The terminal ends 208a-208f may be portions configured to help retain the stent body 200 on a delivery device (e.g., by mating with structures on the delivery device). In some example, one or more terminal ends 208a-208f may be radiopaque or may include radiopaque elements, which may be configured to aid a clinician in visualizing the position of the stent body 200 within a body lumen.

In some examples, the plurality of cells 206a-206f defined by the end segment 204a may alternate about the circumference of the stent body 200 between larger cells 206b, 206d, and 206f and smaller cells 206a, 206c, and 206e. In some examples, the plurality of cells 206g-206i defined by the intermediate segment 204b may be substantially equal in size (e.g., equal or nearly equal). In some examples, the plurality of cells 206j-206o defined by the end segment 204g may alternate about the circumference of the stent body 200 between larger cells 206k, 206m, and 206o and smaller cells 206j, 206l, and 206n.

In some examples, at least one of the end segment 204a and the end segment 204g (e.g., one of the end segments 204a or 204g, or both of the end segments 204a and 204g) may include cells that are each smaller than each of the cells of the intermediate segments 204b-204f.

Each of the cells 206 may define a plurality of peaks and valleys. A peak is a vertex that, together with the adjacent struts 205 forming the vertex, points in a distal or proximal direction away from a longitudinal center of the stent segment comprising the cell. For example, the struts 205b and 205c join at a vertex to form a peak pointing in a proximal direction away from a longitudinal center of the stent segment 204a. As another example, the struts 205f and 205g join at a vertex to form a peak pointing in a distal direction away from the longitudinal center of the stent segment 204a. A valley is a vertex that, together with the adjacent struts 205 forming the vertex, points in a distal or proximal direction toward the longitudinal center of the stent segment comprising the cell. For example, the struts 205a and 205b join at a vertex to form a valley pointing in a distal direction. As another example, the struts 205e and 205f join at a vertex to form a valley pointing in a proximal direction. In some cases, the vertex of a valley may be located at the longitudinal center of the stent segment comprising the cell. For example, the struts 205a, 205b, 205e, and 205f join at a vertex at the longitudinal center of the stent segment 204a, the struts 205a and 205b form at valley pointing in a distal direction, and the struts 205e and 205f form a valley pointing in a proximal direction As with the stent body 100, in some examples, with the stent body 200, larger cells may be defined by more surrounding struts than smaller cells and may define more peaks and valleys than smaller cells.

In some examples, at least one of the end segment 204a and the end segment 204g (e.g., one of the end segments 204a or 204g, or both of the end segments 204a and 204g) may define the same number of peaks and valleys as at least one of the intermediate segments 204b-204f. For example, the intermediate segment 204b and/or any of the intermediate segments 204c-204f, may define only x number of peaks and valleys and the end segment 204a, the end segment 204g, or both of the end segments 204a and 204g, may define only x number of peaks and valleys.

For example, in the illustrated example, each side of each of the intermediate segments 204b-204f (i.e., each circumferential row of struts defining either side of the respective stent segment) defines 24 peaks and valleys, including twelve peaks and twelve valleys, and each side of each of the end segments 104a and 104g defines 24 peaks and valleys, including twelve peaks and twelve valleys.

In some examples, at least one of the end segment 204a and the end segment 204g (e.g., one of the end segments 204a or 204g, or both of the end segments 204a and 204g) may define more cells than at least one of the intermediate segments 204b-204f. For example, the intermediate segment 204b and/or any of the intermediate segments 204c-204f, may define y number of cells and the end segment 204a, the end segment 204g, or both of the end segments 204a and 204g may define at least y+1 number of cells. For example, in the illustrated example, the intermediate segment 204b defines the three cells 206g, 206h, and 206i, the end segment 204a defines the six cells 206a, 206b, 206c, 206d, 206e, and 206f, and the end segment 204g defines the six cells 206j, 206k, 206l, 206m, 206n, and 206o.

The end segments 204a and 204g of the stent body 200 may have different performance requirements than the middle of the stent body 200. For example, the end segments 204a and 204g may be more influential on the ease of deployment of the stent in a body lumen of a patient and/or deployment accuracy compared to the intermediate segments.

The pattern of the cells 206 of the end segments 204a and 204g of the stent body 200 as described herein, which have a different configuration than the intermediate segments of the stent body 200, including a greater number of cells and smaller sized cells (e.g., cells surrounded by fewer struts and including fewer peaks and valleys than the cells of the intermediate segments), than the intermediate segments, may improve ease of deployment and deployment accuracy compared to stents with the same configuration in the end and intermediate segments. For example, the stent may be deployed more smoothly (e.g., may experience less "jump") from a delivery device, such that the stent may be more easily, predictably, and accurately deployed in the intended site within a body lumen without the stent 200 jumping out of the delivery device and away from the intended site.

The pattern of the cells 206 of the end segments 204a and 204g of the stent body 200 as described herein may also accomplish particular technical advantages compared to stents with end segments including the same number of struts but twice the number of evenly sized cells as the intermediate segments. For example, the end segments 204a and 204g may have increased flexibility over such designs without a substantial reduction in radial or lateral forces. With increased flexibility in the end segments 204a and 204g, overlapped stents may have smoother flexibility transitions in a region of overlap and, therefore, improved durability in an overlapped configuration.

Figure 3:
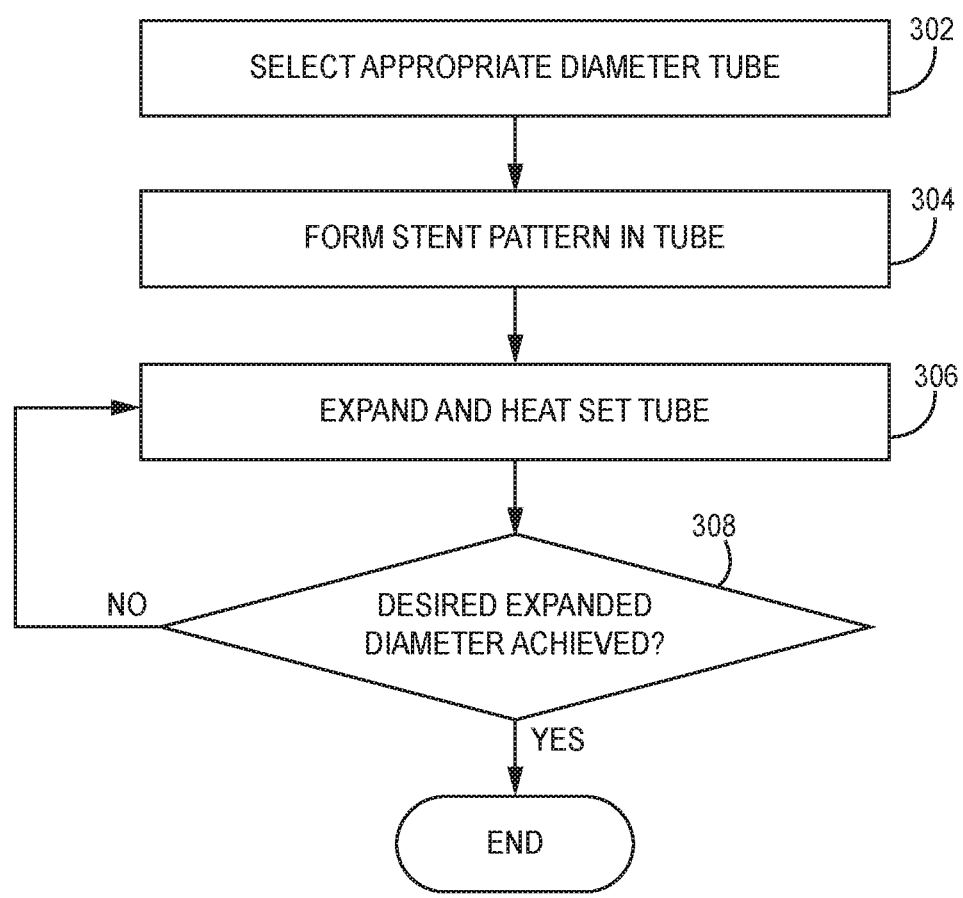
FIG. 3 is a flow diagram illustrating an example method of manufacture of the stents shown in FIGS. 1A-2C.

FIG. 3 is a flow diagram illustrating an example method of manufacture of the stents shown in FIGS. 1A-2C. In accordance this process of manufacture, a tube, such as a nitinol tube having an appropriate defined diameter is selected (302). For a venous application, the stent may require a greater wall thickness relative to arterial stents, e.g., approximately 0.45 mm for the 10, 12 and 14 mm stents and approximately 0.7 mm for the 16, 18 and 20 mm stents. The tube is then positioned with respect to a laser. The laser, which is programmed to provide the stent segment pattern of the stent body 200 or 300 described hereinabove, is activated to form the stent segment pattern (304).

In examples in which the stent is self-expandable and, therefore, formed from a self-expanding material, the cut tube is then subjected to a shape-setting process in which the cut tube is expanded on a mandrel and then heated (306). Multiple incremental expansions and heating cycles may be used to shape-set the stent body 100 or 200 to a desired expanded diameter (308). In some examples, the final expanded diameter may be equal to the desired deployed diameter of the stent body 100 or 200. The stent body 100 or 200 may be axially restrained such that the length of stent does not change during expansion.

Figure 4:
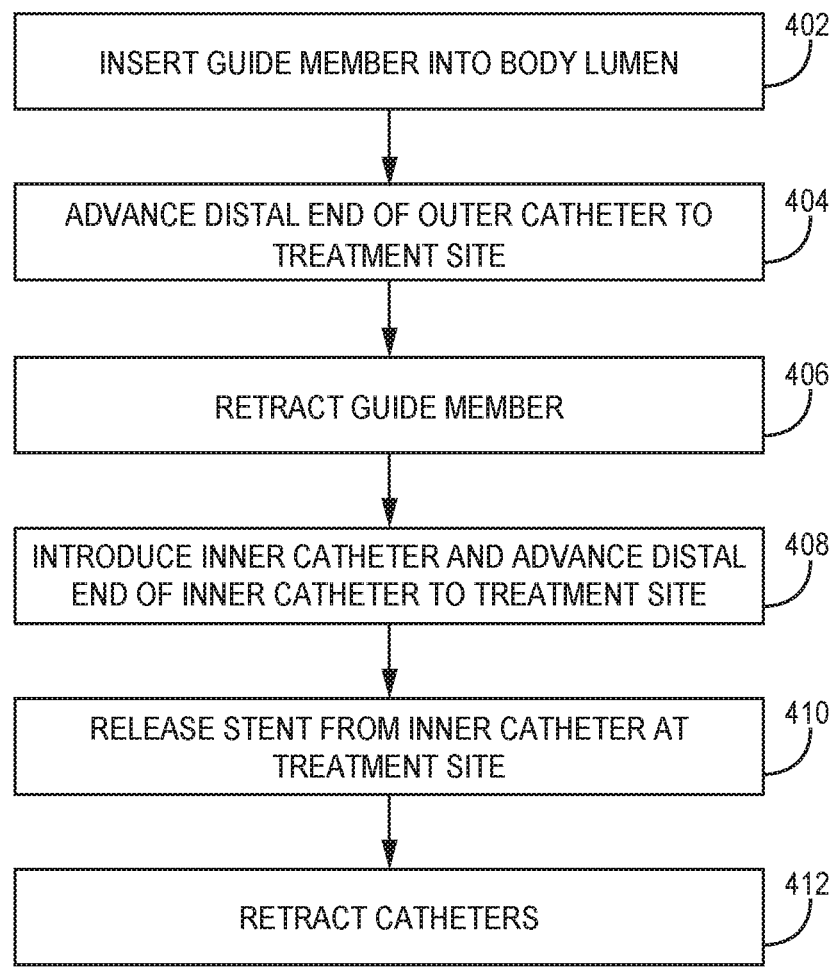
FIG. 4 is a flow diagram illustrating an example method of implanting any one of the stents shown in FIGS. 1A-2C.

FIG. 4 is a flow diagram illustrating an example method of implanting any one or more of the stents shown in FIGS. 1A-2C. A guide member may be introduced into a body lumen of a patient (402). The guide member may be advanced though the body lumen to position a leading end (distal end) of the guide member at a target location as determined by a clinician. In some examples, the guide member may include a guidewire, a guide catheter, or both a guidewire and a guide catheter.

An outer catheter may be introduced over the guide member, or, in some examples, within the guide member, and a distal portion of the outer catheter may be advanced substantially adjacent to the treatment site as determined by the clinician (404). The outer catheter may define an outer catheter lumen.

The guide member may be retracted to remove the guide member from the outer catheter lumen (406), while leaving the outer catheter in place.

In some examples, an inner catheter may be introduced within the outer catheter and a distal portion of the inner catheter may be advanced proximate to the treatment site (408). In some examples, the distal portion of an inner catheter may be advanced to be substantially aligned with the distal portion of the outer catheter. In such examples, a distal portion of the inner catheter may be secured to a stent, including the stent body 100 of FIGS. 1A-1C or the stent body 200 of FIGS. 2A-2C.

In some examples, both the outer catheter and inner catheter may be advanced to the target location simultaneously, with the inner catheter being inside the outer catheter and the stent being positioned between the inner catheter and the outer catheter. For example, the delivery device described in U.S. patent application Ser. No. 14/256,136 naming inventors Senness et al., which is entitled, "STENT DELIVERY SYSTEM" and is incorporated herein by reference in its entirety, may be used to deliver any of the stents described herein. In such examples, the outer catheter may help retain the stent relative to the inner catheter.

The stent may be released from the inner catheter lumen and to the treatment site (410). For example, in some examples, a plunger may be advanced within the inner catheter lumen to push the stent from a distal portion of the inner catheter lumen. A clinician may control the plunger to advance the plunger such that the stent is advanced from the inner catheter.

In other examples, the stent may be positioned between the inner and outer catheters, and the outer catheter may be retracted with respect to the inner catheter and stent to allow for release of the stent from the inner catheter.

As the stent is released from a distal end of the inner catheter lumen or from around an outer surface of the inner catheter, the stent may expand such that it is secured against the wall of the body lumen and anchors the stent within the body lumen.

In other examples, the stent may be expanded via a balloon or other mechanism.

After satisfactory delivery of the stent, other elements, including, for example, the outer catheter, an inner catheter, and/or a plunger may be removed from the body lumen (412).

Various examples have been described. These and other examples are within the scope of the following claims.

What is claimed is:

1. A stent comprising:
    a stent body defining a longitudinal axis and proximal and distal ends, the stent body being expandable from a compressed configuration to an expanded configuration, the stent body including a plurality of stent segments,
    wherein the stent segments include a first end segment and a second end segment on opposite ends of the stent body and at least one intermediate segment disposed between the first end segment and the second end segment,
    wherein each stent segment defines a plurality of cells,
    wherein each stent segment defines a plurality of peaks and valleys, wherein the plurality of cells defined by the first end segment alternate about the circumference of the stent between larger cells and smaller cells, and wherein, for all of the at least one intermediate segments between the first end segment and the second end segment, each cell of the plurality of cells defined by a respective one the at least one intermediate segments is larger than each of the larger cells and the smaller cells defined by the first end segment, wherein the first end segment includes a first circumferential row of struts and a second circumferential row of struts defining each of the larger cells and the smaller cells of the first end segment, the second circumferential row of struts being directly adjacent to the first circumferential row of struts and being between the first circumferential row of struts and the plurality of cells of the at least one intermediate segment, wherein each individual strut of the second circumferential row of struts is connected with an adjacent individual strut of the second circumferential row of struts at a single vertex, and wherein each individual strut of the second circumferential row of struts is substantially straight between respective single vertices connecting the individual strut to respective adjacent struts.

2. The stent of claim 1, wherein all of the cells of the plurality of cells defined by the at least one intermediate segment are substantially equal in size.

3. The stent of claim 1, wherein the at least one intermediate segment defines only x number of peaks and valleys, and wherein the first end segment defines at least x+1 number of peaks and valleys.

4. The stent of claim 3, wherein the first end segment defines only $$\frac{5}{4}x$$

number of peaks and valleys.

5. The stent of claim 3, wherein the second end segment defines at least x+1 number of peaks and valleys.

6. The stent of claim 5, wherein the second end segment defines only $$\frac{5}{4}x$$

number of peaks and valleys.

7. The stent of claim 1, wherein the at least one intermediate segment defines only y number of cells, and the first end segment defines at least y+1 number of cells.

8. The stent of claim 7, wherein the second end segment defines at least y+1 number of cells.

9. The stent of claim 1, wherein the at least one intermediate segment defines only x number of peaks and valleys, and wherein the first end segment defines only x number of peaks and valleys.

10. The stent of claim 9, wherein the second end segment defines only x number of peaks and valleys.

11. The stent of claim 1, wherein the plurality of cells defined by the second end segment alternate about the circumference of the stent between larger cells and smaller cells.

12. The stent of claim 1, wherein the first circumferential row of struts defines a first peak and a first valley, the first peak pointing away from a longitudinal center of the first end segment and the first valley pointing towards the longitudinal center of the first end segment, wherein the second circumferential row of struts defines a second peak and a second valley, the second peak pointing away from the longitudinal center of the first end segment and the second valley pointing towards the longitudinal center of the first end segment, and wherein the first circumferential row of struts and the second circumferential row of struts are connected to each other between the first valley and the second valley.

13. The stent of claim 12, wherein the connection between the first valley and the second valley is at a common vertex of the first valley and the second valley.

14. The stent of claim 12, wherein the at least one intermediate segment includes the second circumferential row of struts and a third circumferential row of struts defining cells of the at least one intermediate segment, the second circumferential row of struts being directly adjacent to the third circumferential row of struts, wherein the third circumferential row of struts includes a third peak and a third valley, the third peak pointing away from a longitudinal center of the intermediate segment and the third valley towards the longitudinal center of the intermediate segment, and wherein the second circumferential row of struts and the third circumferential row of struts are connected to each other between the third valley and an adjacent peak of the second circumferential row of struts.

15. The stent of claim 1, wherein a portion of the first end segment defining one cell of the smaller cells defines only two peaks, only one valley, and only two half valleys, on each of two opposing sides of the portion of the first end segment.

16. The stent of claim 1, wherein the smaller cells defined by the first end segment are smallest cells defined by the first end segment.

17. The stent of claim 16, wherein the larger cells defined by the first end segment are largest cells defined by the first end segment.

18. The stent of claim 1, wherein a portion of the first end segment defining one cell of the smaller cells defines, on each opposing side of the portion of the first end segment, at least two peaks and at least one valley.

19. The stent of claim 1, wherein each individual strut of the second circumferential row of struts have substantially the same length.

20. A method comprising:

forming a stent pattern in a tubular member to form a stent body defining a longitudinal axis and proximal and distal ends, the stent body being expandable from a compressed configuration to an expanded configuration, the stent body including a plurality of stent segments, wherein the stent segments include a first end segment and a second end segment on opposite ends of the stent body and at least one intermediate segment disposed between the first end segment and the second end segment, wherein each stent segment defines a plurality of cells, wherein each stent segment defines a plurality of peaks and valleys, wherein the plurality of cells defined by the first end segment alternate about the circumference of the stent between larger cells and smaller cells, and wherein, for all of the at least one intermediate segments between the first end segment and the second end segment, each cell of the plurality of cells defined by a respective one the at least one intermediate segments is larger than each of the larger cells and the smaller cells defined by the first end segment, wherein the first end segment includes a first circumferential row of struts and a second circumferential row of struts defining each of the larger cells and the smaller cells of the first end segment, the second circumferential row of struts being directly adjacent to the first circumferential row of struts and being between the first circumferential row of struts and the plurality of cells of the at least one intermediate segment, wherein each individual strut of the second circumferential row of struts is connected with an adjacent individual strut of the second circumferential row of struts at a single vertex, and wherein each individual strut of the second circumferential row of struts is substantially straight between respective single vertices connecting the individual strut to respective adjacent struts.

21. The method of claim 20, wherein the tubular member comprises shape-memory material.

22. The method of claim 20, further comprising incrementally expanding and heat setting the tubular member.

23. The method of claim 20, wherein all of the cells of the plurality of cells defined by the at least one intermediate segment are substantially equal in size.

24. The method of claim 23, wherein the second end segment defines at least x+1 number of peaks and valleys.

25. The method of claim 24, wherein the second end segment defines only $$\frac{5}{4}x$$

number of peaks and valleys.

26. The method of claim 20, wherein the at least one intermediate segment defines only x number of peaks and valleys, and wherein the first end segment defines at least x+1 number of peaks and valleys.

27. The method of claim 26, wherein the first end segment defines only $$\frac{5}{4}x$$

number of peaks and valleys.

28. The method of claim 20, wherein the at least one intermediate segment defines only y number of cells, and the first end segment defines at least y+1 number of cells.

29. The method of claim 28, wherein the second end segment defines at least y+1 number of cells.

30. The method of claim 20, wherein the at least one intermediate segment defines only x number of peaks and valleys, and wherein the first end segment defines only x number of peaks and valleys.

31. The method of claim 30, wherein the second end segment defines only x number of peaks and valleys.

32. The method of claim 20, wherein the plurality of cells defined by the second end segment alternate about the circumference of the stent between larger cells and smaller cells.

33. A method comprising:
advancing a distal end of a catheter to a treatment site within a patient, wherein a stent is disposed within the catheter;
releasing the stent from the catheter at the treatment site, the stent comprising:
a stent body defining a longitudinal axis and proximal and distal ends, the stent body being expandable from a compressed configuration to an expanded configuration, the stent body including a plurality of stent segments,
wherein the stent segments include a first end segment and a second end segment on opposite ends of the stent body and at least one intermediate segment disposed between the first end segment and the second end segment,
wherein each stent segment defines a plurality of cells,
wherein each stent segment defines a plurality of peaks and valleys,
wherein the plurality of cells defined by the first end segment alternate about the circumference of the stent between larger cells and smaller cells, and
wherein, for all of the at least one intermediate segments between the first end segment and the second end segment, each cell of the plurality of cells defined by a respective one the at least one intermediate segments is larger than each of the larger cells and the smaller cells defined by the first end segment,
wherein the first end segment includes a first circumferential row of struts and a second circumferential row of struts defining each of the larger cells and the smaller cells of the first end segment, the second circumferential row of struts being directly adjacent to the first circumferential row of struts and being between the first circumferential row of struts and the plurality of cells of the at least one intermediate segment,
wherein each individual strut of the second circumferential row of struts is connected with an adjacent individual strut of the second circumferential row of struts at a single vertex, and wherein each individual strut of the second circumferential row of struts is substantially straight between respective single vertices connecting the individual strut to respective adjacent struts.

34. The method of claim 33, further comprising:
inserting a guide member into a body lumen of the patient; and
advancing the distal end of the catheter to the treatment site over the guide member.

35. The method of claim 33, wherein all of the cells of the plurality of cells defined by the at least one intermediate segment are substantially equal in size.

36. The method of claim 33, wherein the at least one intermediate segment defines only x number of peaks and valleys, and wherein the first end segment defines at least x+1 number of peaks and valleys.

37. The method of claim 36, wherein the first end segment defines only $$\frac{5}{4}x$$

number of peaks and valleys.

38. The method of claim 36, wherein the second end segment defines at least x+1 number of peaks and valleys.

39. The method of claim 38, wherein the second end segment defines only $$\frac{5}{4}x$$

number of peaks and valleys.

40. The method of claim 33, wherein the at least one intermediate segment defines only y number of cells, and the first end segment defines at least y+1 number of cells.

\* \* \* \* \*